United States Patent [19]
Santilli et al.

[11] Patent Number: 4,940,066
[45] Date of Patent: Jul. 10, 1990

[54] TIBIA RETRACTOR

[76] Inventors: Albert N. Santilli, 2832 Gates Mills Blvd., Cleveland, Ohio 44124; Kenneth M. Kuzmick, 5601 Corporate Way, W. Palm Beach, Fla. 33407

[21] Appl. No.: 273,384

[22] Filed: Nov. 17, 1988

[51] Int. Cl.$^5$ .............................................. A61F 5/40
[52] U.S. Cl. ..................................... 128/882; 272/96
[58] Field of Search ............... 269/328, 322; 128/882, 128/20, DIG. 15, 82, 80 R, 80 L, 883, 845; 272/96, 139

[56] References Cited

U.S. PATENT DOCUMENTS

| Re. 32,680 | 5/1988 | Pompa | 128/882 |
|---|---|---|---|
| 2,467,943 | 4/1949 | Mikell, Jr. | 272/139 |
| 4,091,808 | 5/1978 | Nelson | 128/882 |
| 4,136,858 | 1/1979 | Petersen | 269/328 |
| 4,209,012 | 6/1980 | Smacker | 128/882 |
| 4,407,277 | 10/1983 | Ellison | 128/882 |

OTHER PUBLICATIONS

"Knee Prop for Knee Surgery", devised by James L. LeNoir, M.D., 1953, and described in Nov. 1988, *Orthopedic Review*.
"Alvarado Surgical Knee Holder", Model 1320, as described in the *Alvarado Orthopedic Research Products Catalogue*, p. A177.

Primary Examiner—Edward M. Coven
Assistant Examiner—M. Graham
Attorney, Agent, or Firm—Weston, Hurd, Fallon, Paisley & Howley

[57] ABSTRACT

A tibia retractor includes a receptacle into which one's foot can be placed. The receptacle can be adjusted to attain a tight-fitting relationship between the foot and the receptacle. A strap extends from one side of the receptacle and is connectable to the other side of the receptacle. The strap is long enough to pass over the femur so that, when the strap is secured in place, the tibia will be held in a fixed position relative to the femur.

17 Claims, 2 Drawing Sheets

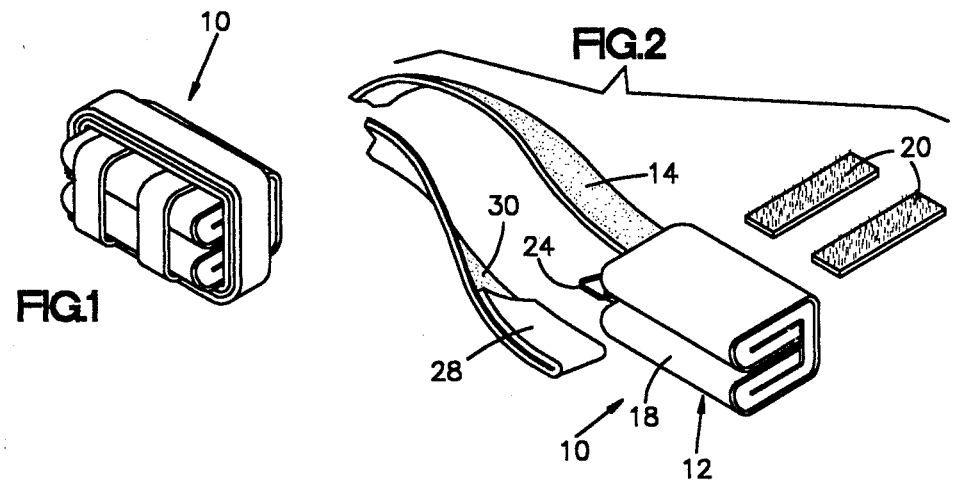
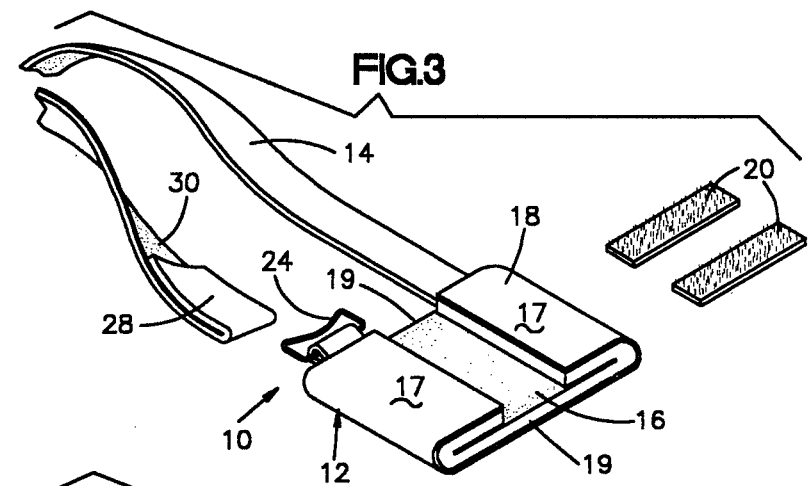
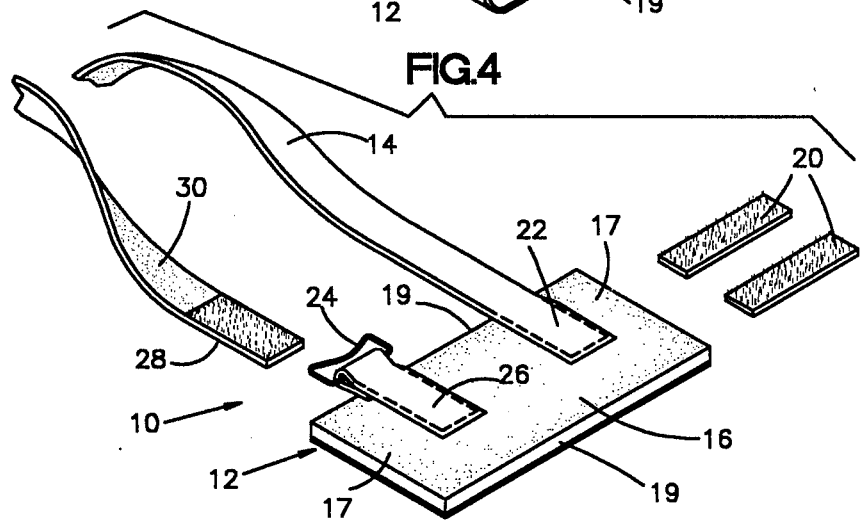

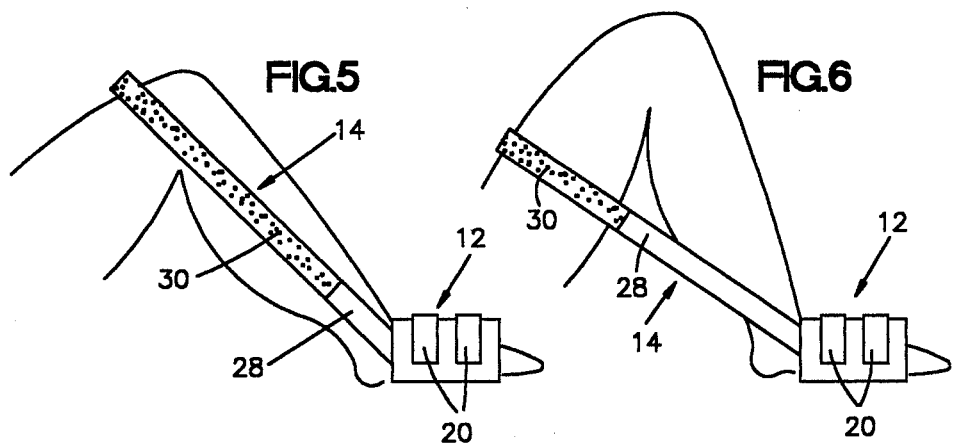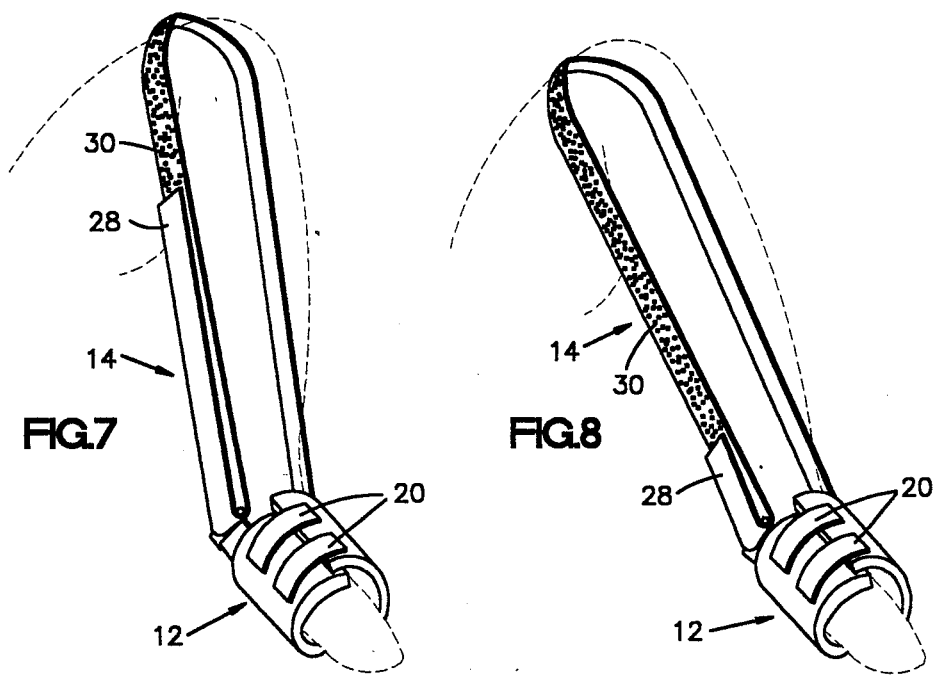

TIBIA RETRACTOR

BACKGROUND OF THE INVENTION

1. Field of the Invention

The invention relates to techniques for immoblizing one's leg for purposes of surgery 2. Description of the Prior Art In the course of conducting surgery on the legs, it is necessary that they be properly positioned and held in place without movement until the operation has been completed. In the particular case of knee implant/arthroplasty surgery, it is necessary that the knee be held in a fixed position for a certain period of time, and then moved to one or more additional fixed positions for additional periods of time.

Typically, the patient is placed on his back and the knee is elevated. The knee is positioned as desired by placing the foot on the operating table and moving the foot toward or away from the patient's body so that the knee is flexed properly. After a proper flexed position has been attained, the foot must be firmly held in place until another knee position is required The conventional technique for positioning the knee as described is a manual one, that is, one of the surgeon's assistants holds the patient's foot in whatever proper position is necessary throughout the entire course of the operation.

A drawback of the conventional knee-positioning technique is that it requires the full-time efforts of an assistant to maintain the knee in its proper position. Moreover, because the technique is entirely manual, it can happen that the position of the foot will slip from time to time, thereby increasing the chance that damage to the knee will occur. An additional drawback of the described technique is that the chances of infection are increased due to the presence of another person in the operating room at a position near the site of the operation.

Desirably, a technique would be available for fixing the knee in any desired position during the course of an operation. The technique should be inexpensive, reliable, capable of permitting the knee to be adjusted to any desired position, and it should minimize the chances of infection.

SUMMARY OF THE INVENTION

The present invention overcomes the foregoing difficulties of the prior art and provides a new and proved technique for positioning one's leg during a surgical operation. The present invention is particularly adapted to knee operations, although it is not so limited.

The technique according to the invention involves retracting the tibia, because proper positioning of the tibia ensures proper positioning of the remainder of the leg for purposes of the operation. A tibia retractor according to the invention includes a flexible planar member having first and second opposed sides disposed generally parallel to each other and first and second opposed ends disposed generally parallel to each other. The first and second sides are foldable toward each other to form a receptacle into which the foot can be placed. The first end of the planar member is disposed closest to the ankle and defines a first portion of the receptacle, and the second end of the planar member is disposed closest to the toes and defines a second portion of the receptacle. The receptacle is adjustable so as to attain a tight-fitting relationship between the foot and the receptacle by establishing substantial surface-to-surface contact between the foot and the receptacle. An extensible strap having first and second ends is connected at each end to the first portion of the receptacle on either side of the ankle. The strap is of such a length that the strap passes over the femur when the first end of the strap is connected to the second portion of the receptacle and the foot is disposed within the receptacle. The strap is provided with a connecting means for releasably connecting the second end of the strap to the first portion of the receptacle such that the strap can be securely connected to the receptacle in a variety of lengths, thereby permitting the effective length of the strap to be adjusted. In turn, the position of the tibia relative to the femur can be adjusted, and with it the position of the knee.

In the preferred embodiment, the receptacle is in the form of a planar, flexible member that can be folded into a generally cylindrical shape and secured there by means of releasable hook and loop fasteners such as VELCRO tabs. The strap is an elongate member that includes at its free end a releasable fastener in the form of a hook and loop fastener end portion. The first portion of the receptacle preferably includes a rigid loop through which the strap can be fitted. By folding the end of the strap back upon itself and attaching the hook and loop fastener end portion to the strap, the effective length of the strap can be adjusted conveniently.

By using the tibia retractor according to the invention, the surgeon can position the patient's leg without assistance to attain and maintain a desired inflection of the knee merely by securing the end portion of the strap as described. By releasing the end portion and moving it relative to the strap, the position of the leg can be adjusted as necessary during the course of the operation. The tibia retractor according to the invention is inexpensive and, due to its flexible nature, comfortable for the patient. The tibia retractor according to the invention can be sterilized easily, thereby minimizing the possibility of infection. Due to its inexpensiveness, it is expected that the tibia retractor will be discarded after use.

The foregoing and other features and advantages of the invention will be apparent from reviewing the following description and claims, taken in conjunction with the accompanying drawings.

DESCRIPTION OF THE DRAWINGS

FIG. 1 is a perspective view of a tibia retractor according to the invention, the retractor being illustrated in a folded position as provided to the user;

FIG. 2 is a view similar to FIG. 1 showing the tibia retractor in a partially unwrapped position;

FIG. 3 is a view similar to FIG. 2 showing the tibia retractor in a still further unwrapped position;

FIG. 4 is a view similar to FIG. 3 showing the tibia retractor in a completely unwrapped position;

FIGS. 5 and 6 are schematic, side elevational views of the tibia retractor according to the invention as it is used in practice; and, FIGS. 7 and 8 are schematic perspective views similar to FIGS. 5 and 6 showing the tibia retractor in use.

DESCRIPTION OF THE PREFERRED EMBODIMENT

A tibia retractor according to the invention is illustrated in FIGS. 1–4 of the drawings and is identified by the reference numeral 10. The tibia retractor 10 includes a receptacle 12 to which a strap 14 is connected along one side.

The receptacle 12 is in the form of a flexible member defined by a planar, generally rectangular sponge-like member 16. The member 16 includes first and second opposed sides 17 disposed generally parallel to each other and first and second opposed ends 19 disposed generally parallel to each other. A flexible backing member 18 is secured to the sponge-like member 16 by any suitable technique such as gluing. Preferably, the sponge is fabricated from an open cell polyurethane material, while the backing member is formed from a synthetic cloth made from polypropylene, nylon, or the like. The backing member 18 is provided with a plurality of loops. The receptacle 12 also includes a pair of tabs 20. As illustrated, the tabs 20 are in the form of removable, generally rectangular VELCRO strips having a plurality of hooks on one surface. Together, the backing member 18 and the tabs 20 define hook and loop fasteners that enable the sides 17 to be connected to each other.

The strap 14 includes a first end 22 that is connected to the first portion of the receptacle 12. Typically, the connection will be made by sewing through both the sponge-like member 16 and the backing member 18. A rigid loop 24 also is connected to the receptacle 12 by means of a short strap 26. The strap 26 is connected to the receptacle 12 by any suitable technique such as sewing. The strap 14 includes a second end defined by a VELCRO end portion 28 having a plurality of hooks on one surface. The remaining portion of the strap includes a plurality of loops 30 on that side of the strap 14 facing the hook-containing surface of the VELCRO end portion 28.

In use, and particularly referring to FIGS. 5-8, the opposed sides 17 of the receptacle 12 are folded toward each other over the patient's foot. The opposed ends 17 are secured in place by means of the tabs 20. The tabs 20 are pulled tight enough so that a tight-fitting relationship is created between the foot and the receptacle 12 by establishing substantial surface-to-surface contact between the foot and the receptacle 12. After the receptacle 12 has been fitted to the foot as described, the strap 14 is passed over the femur and the end 28 is inserted through the loop 24. The surgeon then positions the tibia as desired in order to attain and maintain a desired inflexion of the knee. Thereafter, the end portion 28 is folded back upon itself and secured against the loops 30.

In FIGS. 5 and 8, the strap 14 is shown in an extended position where the tibia also is extended. In FIGS. 6 and 7, the strap 14 is shown in a retracted position where the tibia also is retracted. By appropriately positioning the end 28 relative to the remainder of the strap 14, the position of the leg can be adjusted as desired.

As is apparent from the foregoing description, the tibia retractor 10 according to the invention is exceedingly inexpensive. It is expected that the retractor 10 will be discarded after use. It also will be appreciated that the retractor 10 can be sterilized without difficulty, thereby minimizing the chances of infection occurring during the course of an operation. Furthermore, due to the flexible, resilient nature of the receptacle 12 and the strap 14, the retractor 10 will not cause discomfort for the patient even during the course of an extended operation.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A tibia retractor, comprising:
a flexible planar member having first and second opposed sides disposed generally parallel to each other and first and second ends disposed generally parallel to each other, the first and second sides being foldable toward each other to form a receptacle into which one's foot can be placed, the first end of the planar member defining a first portion of the receptacle adapted to receive the foot, and the second end of the planar member defining a second portion of the receptacle;
means included as part of the receptacle for attaining a tight-fitting relationship between the foot and the receptacle;
an extensible strap means having first and second ends, the strap means being connected at its first end to the first portion of the receptacle and being connectable at its second end to the first portion of the receptacle, the first and second ends of the strap being connected to opposite sides of the first portion, the strap means for passing over the femur when the second end of the strap means is connected to the first portion of the receptacle and one's foot is disposed within the receptacle; and
connecting means for releasably connecting the second end of the strap means to the first portion of the receptacle, the connecting means permitting the strap means to be securely connected to the receptacle in a variety of lengths, whereby the effective length of the strap means can be adjusted.

2. The tibia retractor of claim 1, wherein the receptacle is in the form of a generally cylindrical shape, the flexible member being generally rectangular when unfolded.

3. The tibia retractor of claim 2, wherein the means included as part of the receptacle for attaining a tight-fitting relationship between the foot and the receptacle is in the form of hook and loop fasteners that connect the first and second sides of the flexible member.

4. The tibia retractor of claim 2, wherein the flexible member includes a sponge-like portion to which a flexible backing member is secured.

5. The tibia retractor of claim 1, wherein the first portion of the receptacle includes a rigid loop through which the second end of the strap means extends.

6. The tibia retractor of claim 1, wherein the connecting means is in the form of a hook and loop fastener end portion that can be folded back upon itself.

7. A tibia retractor, comprising:
a receptacle into which one's foot can be placed, the receptacle being formed from a generally rectangular, planar, flexible member that can be folded into a generally cylindrical shape having first and second end portions, the flexible member having first and second opposed sides, and first and second opposed ends that define the first and second end portions of the receptacle;
means for joining the opposed sides to attain a tight-fitting relationship between the foot and the receptacle;

an extensible strap means having first and second ends, the strap means being connected at the first end to the first end portion of the receptacle and being connectable at the second end to the first end portion of the receptacle, the first and second ends of the strap means being connected to the first end portion at spaced locations, the strap means for passing over the femur when the second end of the strap means is connected to the first end portion of the receptacle; and, the strap means including a hook and loop fastener end portion for releasably connecting the second end of the strap means to the first end portion of the receptacle, the hook and loop fastener end portion permitting the strap means to be securely connected to the receptable in a variety of lengths, whereby the effective length of the strap means can be adjusted.

8. The tibia retractor of claim 7, wherein the first end portion of the receptacle includes a rigid loop through which the second end of the strap means extends for folding back upon itself.

9. The tibia retractor of claim 7, wherein the flexible member is defined by a sponge-like portion to which a flexible backing member is secured.

10. The tibia retractor of claim 7, wherein the means for joining the opposed sides is in the form of hook and loop fasteners.

11. The tibia retractor of claim 10, wherein the flexible backing member includes loop portions that cooperate with hook portions included as part of the hook and loop fasteners.

12. The tibia retractor of claim 1, wherein the means included as part of the receptacle for attaining a tight-fitting relationship between the foot and the receptacle establishes substantial surface-to-surface contact between the foot and the receptacle.

13. The tibia retractor of claim 7, wherein the means for joining the opposed sides establishes substantial surface-to-surface contact between the foot and the receptacle.

14. A method of positioning a patient's tibia to attain and maintain a desired inflection of the knee, comprising the steps of:

providing a receptacle into which the patient's foot can be placed, the receptacle being formed from a flexible planar member having first and second opposed sides disposed generally parallel to each other and first and second ends disposed generally parallel to each other;

providing a strap having first and second ends, the strap being connected at the first end to the first end of the planar member and being connectable at the second end to the first end of the planar member at a location spaced from the first end of the strap;

wrapping the planar member about the patient's foot by bringing the first and second sides toward each other to attain a tight-fitting relationship between the foot and receptacle, the planar member being positioned such that the first end of the planar member is disposed adjacent the patient's ankle;

securing the planar member in place about the patient's foot to maintain substantial surface-to-surface contact between the foot and the receptacle;

passing the strap over the femur;

positioning the tibia such that a desired inflection of the knee is attained; and connecting the second end of the strap to the first end of the receptacle.

15. The method of claim 14, further comprising the steps of:

loosening the second end of the strap and repositioning it relative to the receptacle in order to change the position of the patient's tibia and so that another desired inflection of the knee is attained; and reconnecting the second end of the strap to the first end of the receptacle.

16. The method of claim 14, wherein the step of securing the planar member is accomplished by the use of hook and loop fasteners.

17. The method of claim 14, wherein the step of connecting the second end of the strap is accomplished by the use of a hook and loop fastener.

* * * * *